United States Patent
Orofino

(10) Patent No.: US 9,254,250 B1
(45) Date of Patent: Feb. 9, 2016

(54) MOLECULES TO PERFECT HBA1C LEVELS

(75) Inventor: Donald P Orofino, Port Washington, NY (US)

(73) Assignee: Neville Pharmaceutical, Inc., Albany, NY (US)

( * ) Notice: Subject to any disclaimer, the term of this patent is extended or adjusted under 35 U.S.C. 154(b) by 191 days.

(21) Appl. No.: 13/570,382

(22) Filed: Aug. 9, 2012

Related U.S. Application Data

(60) Provisional application No. 61/521,747, filed on Aug. 9, 2011.

(51) Int. Cl.
*A61K 31/12* (2006.01)
*A61K 8/36* (2006.01)
*A61K 31/185* (2006.01)

(52) U.S. Cl.
CPC ............... *A61K 8/36* (2013.01); *A61K 31/185* (2013.01)

(58) Field of Classification Search
CPC .................................................. A61K 31/12
See application file for complete search history.

(56) References Cited

U.S. PATENT DOCUMENTS

| | | | |
|---|---|---|---|
| 4,557,927 A * | 12/1985 | Miyake et al. | 424/48 |
| 5,569,670 A * | 10/1996 | Weischer et al. | 514/440 |
| 5,840,705 A * | 11/1998 | Tsukada et al. | 514/43 |
| 2005/0019435 A1* | 1/2005 | Young | 424/756 |
| 2006/0025476 A1* | 2/2006 | Antosh et al. | 514/546 |
| 2009/0093502 A1* | 4/2009 | Peters et al. | 514/263.31 |

OTHER PUBLICATIONS

Leclercq-Meyer (Lab of Exp Med, 27(11), 1995, pp. 477-481).*
Tamamogullari et al (Journal of Diabetes and Its Complications 1999; 13:251-253).*

* cited by examiner

*Primary Examiner* — Benjamin Packard
(74) *Attorney, Agent, or Firm* — Thomas A. O'Rourke; Booner & O'Rourke, LLP

(57) ABSTRACT

This invention is of particular use to patients with Diabetes Mellitus. It uses alkyl analogs of the methyl pyruvate (MP) family to provide energy and improve insulin and glucose homeostasis via accelerated intracellular delivery of protons and ATP from each MP. The energy upregulates cellular cross talk and networking resulting in a surge of ATP enabling NADH (via glycolysis) that enables pancreatic islet cells to obtain increased ATP allowing excess insulin manufacture. This process improves cellular respiration and expedites protein, lipid and hormone manufacture. The increased energy also enables telomeres and delays Hayflick limit. Instead of cellular repair, silence, or apoptosis, energy is allocated for cell/organ function. This invention curbs inflammation and ROS by idealizing cellular respiration and diminishing hyperglycemia. In turn a reduction of advanced glycation end products (AGEs), lessened target RNA and nucleic acid toxins, i.e., diminished HbA1c occurs. By decreased drain of cellular energy, genomic function improves.

30 Claims, No Drawings

MOLECULES TO PERFECT HBA1C LEVELS

CROSS-REFERENCE TO A RELATED APPLICATION

This application claims the benefit of U.S. Provisional Patent Application No. 61/521,747, filed Aug. 9, 2011, the full disclosure of which is incorporated by reference.

BACKGROUND OF THE INVENTION

Diseases such as diabetes mellitus (DM), occur at the cellular level and are inflicted by insufficient energy required to continuously maintain the structure and function of cells, particularly in the pancreas. All cells with depleting energy supplies are less capable of their genetically programmed performances, and in this case defective insulin capabilities. Further compounding this cellular malfunction we know the receptor sites, i.e., glucose transporters (Glut4) are down regulated. Now, the increasing glucose enables toxic oxidation and inflammatory compounds to further impair cellular function at the cytosolic and nuclear levels; this creates a need for repair or replacement of these cells. Energy required via the CAC cycle is critically required at this point lest we have further reduction of the VAMP and diminishing mitochondrial numbers. In man, a cell functions alone or in composite utilizing all its energy for these genomic processes. If the cell requires repair, the primary function of the cell is diminished with repair requiring a portion of the cell's total energy. If the repair is significant, all cross talk and synchronization of cell networking is diminished and cell function may stop until repair is effected unless gene silencing or apoptosis intervenes.

From this point forward the use of methyl pyruvate (MP), ethyl pyruvate (EP) and their manifold alkyl analogues (bimethylated and ethylated composites and methyl-ethyl composites of pyruvate) solely or in any and all combinations will be represented by MP as their template for the energy and anti-inflammation needed to resolve the above scenario. Additionally, HbA1c is a protein of hemoglobin in the RBC that irreversibly attaches to plasma glucose for the three-month life span of the RBC. The percent of HbA1c correlates with blood glucose levels that measure: normals from four (4%) percent to six (6%) percent and diabetics at ≥six (6%) percent.

Methyl pyruvate performs as a lipophilic antisense-like bullet that penetrates cell membranes, mitochondrial membranes and nuclear membranes with its active and passive delivery of energy via protons, adenosine triphosphate manufacture (ATP) and methylation. This energy delivering metabolic bullet upregulates all cytosolic and nuclear capabilities. It can even negate messenger RNA (mRNA) expression. Now, because of instant protons and pyruvate delivered, there is immediately empowered glycolysis and/or CAC production of ATP and the cell functions with more efficient performance. Through this newly available energy, gene silencing can be reversed, repairs completed, apoptosis performed, and the cell is upgraded and/or divides (cell partitioning) into a new and improved cell having shed its prior oxidative cellular/genetic debris. In DM this means improved Glut4 networking, improved insulin sensitivity, increased intra and intercellular networking and increased superoxide dismutase (SOD) production. Further, due to MP, many nutrients and complicit molecules including peroxisome proliferator-activator receptor (Ppars) will now function more effectively and efficiently, i.e. as infused and increased cellular energy can now effect niacinamide (B3) and nicotinamide adenine dinucleotide (NAD) at an intracellular level that enables and protects beta cell function. In addition, energy reduces the level of HbA1c, increases cell life span and prepares FOXO3a to stop proteolysis initiation, and/or initiate apoptosis when and where appropriate in the cell cycle. Methylation ability afforded by MP assists in cellular methylation but can also afford to enhance gene expression as it retracts the histone sheath of the chromatin allowing increased genetic expression. With all vitamins, all amino acids, all nutrients, hydronium ion and water transport, all cation and anion channel functions, lipid metabolism, protein metabolism, glucose metabolism, organ functioning, genomic protection replication and functioning, MP enables all of these individual physiologic roles and applications. (Ethyl and Methyl pyruvates have been tested in human volunteers and have been shown to be safe in clinically prescribed doses.)

OBJECTS OF THE INVENTION

It is an object of the invention to administer a therapeutically effective amount of methyl and/or ethyl pyruvate to a patient suffering from Diabetes Mellitus in order to provide extra corporeal and CAC ready energy to the cells of the patient for restoring the patient's cellular function.

It is another object of the invention to specifically increase cellular ATP through the administration of methyl and/or ethyl pyruvate.

It is still another object of the invention to up regulate and restore specific cellular function through the increased cellular ATP.

It is a further object of the invention to diminish cellular inflammation and reverse the cellular disease process, i.e., energy deprivation, in a patient afflicted with Diabetes Mellitus.

It is an even further object of the invention to regulate HbA1c levels by allowing cells to better manufacture insulin.

BRIEF SUMMARY OF THE INVENTION

The methyl pyruvate molecule and certain of these molecular analogues are lipophilic antisense-like permeants, each of which holds onto its own membrane penetrability as well as acting collectively to produce a timed release delivery within the inner mitochondria. The combinational synergy can be different than each effect individually. MP and the analogues increase insulin in the animal model six-fold within the islet cells. This up regulation is key for enhanced utilization and regulation of glucose transport. MP closes potassium channels and opens calcium channels (via aquaporin generation) allowing a more favorable cellular milieu (increases cytosolic pH) that increases CAC productivity via our delivered MP (as pyruvate), as well as the now utilizable glucose. The use of MP and/or EP as energy molecules allows gene silenced and disabled apoptotic cells to proceed logically/genomically to a more idealized homeostatic state for the organism. The invention represents a method for genomic self-regulation of HbA1c.

This increased insulin production and glucose utilization reduces target nucleic acids, and/or proteins such as HbA1c, directly enabling improved therapeutic outcomes. Because of the active and passive energy delivery by this molecule, all intracellular and intranuclear functions are upgraded and rebooted with enhanced intracellular crosstalk and signaling; the genome is also rebooted in an enhanced manner. Now, the more efficient genomic guidance allows improved glucose control that disarms oncoming debilitating diseases from getting a foothold; energy stays the upregulation of all cellular function that cannot allow cellular deterioration. The same guidance mechanism demonstrates certain esters of pyruvate have pharmaceutical effects such as reducing the inflammatory response. Also, MP and analogues engender mitochondrial expression that enacts changes via the nuclear genomic creation of these sustaining organelles which provide upstream molecular regulators: the master regulators being peroxisome proliferator-activated receptor gamma, coactivator 1 alpha (PGC1a) and activated protein kinase (AMPK). Their targets homeostatically and instantly recalibrate from PGC1a and AMPK with the downstream signaling molecules coming from the activities of SIRTS, FOXO, CAMP, CREB, CREM and PPARs. Their communication and crosstalk enable a synchrony of NADH/NAD/FAD/Acetyl fuel/PO4 regulation, as well as glycolysis with its electron and proton transfer (malate-aspartate shuttle) and gradient energy balancing cellular requirements each and every picosecond with all the above molecules and their networking. As energy is transferred from the MP through the nuclear membrane, the nuclear superfamily of transcriptionally regulated genes can be more successfully deployed, just as it also occurs with mitochondrial cristae penetration by protons, as evidenced by Jurkat voltage change enabling enhanced mitochondrial function and reproduction. The upregulating of cellular energy and receptor sites by the present invention in all viable cells enables increased functional efficiency under physiologic or pathologic challenge. In addition, the present invention is further a unique and selective PPAR agonist.

In the subpopulation with HbA1c elevations greater than 6.0, PGC1a is decreased, thereby diminishing the cells restorative capability every picosecond until the upstream and downstream molecular crosstalk lessens or disappears and cellular function goes on hold for repair. Further, PGC1a's continuing decrease creates cell malfunction until cell silencing or apoptosis occurs. Every molecule needed for upstream-downstream constant cellular energy balance and genomic homeostasis demands specific energy requirements for their nuclear and cytosolic organelles' creation and sustenance. Less energy yields less genomic expression with constantly diminished cellular capabilities, then cellular default occurs. The present invention reduces elevated glucose levels by causing the biochemical reduction of posttranslational phosphorylation of FOX01, 3a, and 4. This change engenders nuclear translocation of these proteins which causes a reduction in gluconeogenesis—a reduction in blood glucose load.

DETAILED DESCRIPTION OF INVENTION

In the treatment of DM MP can be administered depending on the clinical/life situation in the following dosages: 1 microgram to 50 grams per day. The dosages are may be administered by any suitable manner including but not limited to orally, transdermally or intravenously.

Twelve patients with DM, including a juvenile diabetic in her fifth decade, took two (2) grams of MP in water two (2) times per day without any other lifestyle change. The average decrease of HbA1c was one percent (1%). (The group average HbA1c diminished from 7.5% to 6.5% during the course of three (3) months of treatment.)

No other new treatment, other than MP and EP, need be applied in this invention's application for diabetics. At a dose PO of two (2) grams of MP diluted in water at one (1) gram per liter given one (1) or more times per day as an organic ester/enol existing as a tautomeric molecule and at times a Zwitterion, delivers energy to cells and initially circumvents the usual prior preparation via glycolysis, fermentation, CAC, or any other cellular manufacturing energy systems. It starts or augments cellular energy that now more easily perpetuates itself with greater efficiency. MP and EP are lipophilic molecules that traverse cellular barriers within the human body. "MP" and "EP", as used herein, refer to all tautomeric and charged forms of the compounds.

All cytosolic and nuclear structures are targets of these molecules that deliver premanufactured protons and pyruvate fuel for the CAC cycle that bypasses any prior cellular/mitochondrial preparation. This free energy upregulates impaired genomic functions. The methyl group, a proton donor, boosts genomic expression both genetically and epigenetically by its effect on the histone sheath that now further allows enhanced gene expression. This energy beneficially effects RNA editing (RNAi) of cellular function enabling enhanced genetic expression: in this case Glut4 networking and Atk upregulating. Energy supplied and perpetuated by MP delivered intracellularly increases manufacture of proteins, lipids and hormones via the mRNA at the ribosomes of the endoplasmic reticulum. MP as a prototype of the alkyl esters of pyruvate requires no preparation to start the CAC cycle at the pyruvate-AcetylCoA juncture. The resultant energy cascade causes further production of ATP, NADH, NAD(P)H, GTP and FADH thus engendering the energy cycles needed for cellular homeostasis and/or upregulating the genome through RNA editing.

MP and the alkyl analogs are small concise permeant molecules that seamlessly penetrate the outer and inner membranes of mitchondria (TOM and TIM) for nutrient delivery. Similarly, MP and analogs easily penetrate nuclear membranes now allowing utilization as an epigenetic tool for enhancing translational and transcriptional messaging.

A cell from inception has diminishing efficiency of energy production with its increasing toxin manufacture thereby diminishing energy that would have engendered a more ideal genomic expression. As a result of decreasing energy production cell function is compromised and the cell must repair/detoxify itself and/or gene silencing occurs with further energy depletion; and if this disease (energy lack) predominates then apoptosis/autophagy consumes the genome. The specific direction a cell takes closely correlates with the totality of its energy production. Disease and aging impairs the cells ability to produce sufficient energy to neutralize and remove toxic wastes. Decreased energy causes aging and disease. Normally cellular respiration expires H2O and CO2. Normally, cell functions should be performed without toxicity or depletion. Decreasing energy mitigates this "normal" perfection. As a consequence disease is created and genomic destruction ensues.

MP instilled into pancreatic rat islet cells enable upregulation of insulin manufacture six-fold in several studies. The measured Jurkat current is countered and neutralized by MP's proton impedance enhancing its later provocation in increased insulin manufacture.

Since diabetic cells are energy deprived this further decreases cellular energy production, transference and storage; necessary cell signaling molecules and VAMP for nuclear-cell membrane cross-talk and work continue to diminish and disappear. A void of energy for the production of these proteins is created. Likewise in this weakened cell, oxidative stress engenders increased ROS allowing further multi-system impairments with both intracellular and extracellular toxicity resulting in glycation end products (HbA1c) in addition to peroxinitrates, hydroxyls, singlet oxygen, etc. This result induces increased iron presence that further induces oxidative stress. Target receptor cells lacking specific VAMP transporters and cell membrane receptor sites become increasingly insulin resistant further reducing intracellular transport with diminished cell signaling and cross-talk. The scaffolding and substance of the cytosolic and nuclear fabric becomes depleted with myriad functions put on hold or ended lest the cell can find a new and improved source of energy to reboot thousands of cellar and nuclear pathways (i.e. GLUT4).

The use of these small lipophilic permeant compounds reduces glycated proteins (HbA1c) because of the energy provided that diminishes the manufacture of ROS, glycosylation and toxic byproducts. As a result, through restored energy propagation, cellular function strengthens significantly allowing restoration of organelles and anti-inflammatory compounds yielding idealized genomic expression and cellular rejuvenation.

This invention may be administered two (2) times per day as mixed: one (1) gram MP/liter water with incremental dosages under supervision. Glucose monitoring in diabetics and people with co-morbid conditions is advised, even though this is a generally regarded as safe (GRAS) molecule. In addition, pre-diabetics and hypoglycemic situations require glycemic monitoring and appropriate medical countenance. In non-diabetics the glucose should range from >60 mg % to 150 mg % (at rest). In diabetics, sugar range is 50 mg % + or − from the pre-treatment baseline levels and should be under medical supervision (at rest).

Ranges for the administration of a therapeutically effective amount of methyl and/or ethyl pyruvate may be from about 1 microgram to about 100 grams per day. A preferred range may be from about 1 microgram top about 50 grams per day in divided doses. A more preferred range may be from about 1 gram to about 10 grams per day. A most preferred range may be from about 1 gram to about 4 grams per day in eight ounces of water per gram of methyl pyruvate. In addition, the administration may be daily, weekly, life long, pro re nata (PRN), etc. The frequency of administration may be affected by the physiological need of the patient.

The ethyl pyruvate is preferred to be administered 1 to 2 grams per day in water at a concentration of 1 gram of ethyl pyruvate per 1 liter of water. The ethyl pyruvate, as disclosed above, may be administered daily, weekly, monthly, lifelong, PRN, etc. I.V. dosages for ethyl pyruvate are ≥90 milligrams/kilogram per day and up to 200+ grams per day in divided oral dosaging.

The present invention is a way of linking NAD metabolism and signaling to the control of cellular functions. Further, the present invention is a way of directly linking to and therefore modulating SIRTS dependent regulation of chromatin transcription. Even further, the present invention represents a method of selective RNA editing. Still even further, the unique energy delivery system of the present invention provides a method of changing the RNAi binary (off/on) switch of the transcriptional code being expressed by mRNA with its interaction of RNAi (silencing) at the RNA upstream site (most common) or even at the translational gene DNA site (less likely). The present invention also reverses insulin resistance as a byproduct of increasing cell energy. In addition, the pharmacological capability and function of many pharmaceutical ligands that require energy to focus is enhanced which enables its function and diminishes its toxicity once inside the cell.

The dosages of the present invention may be dependent on factors relating to the patient, such as but not limited to comorbid disease, BMI, and/or activity level. The dosage may vary by 2 orders of magnitude depending in response to these factors.

In addition, the methyl and/or ethyl pyruvate may be administered with at least one additional agent wherein the agents include at least one of alpha lipoic acid, magnesium chloride, acetyl L carnitine, taurine, Inosine, magnesium L-theonate, vitamin D3, medium chain triglycerides, vitamin E in the form of d-alpha and gamma tocopherol, and/or niacin.

The routes of administration of the methyl pyruvate and/or ethyl pyruvate can:
 a. be provided in a micronized, freeze-dried powder;
 b. be along with added cofactors, can be individually provided
  in a powder packet and added to water or other beverages, such as but not limited to a sports or energy drink;
 c. be provided as a frozen desert;
 d, be provided as an oral gel mixture;
 e. be incorporated into a gum base and used with
  hard-shelled immediate and time-released delivery mechanism (chicklets);
 f. be provided as a time-released transdermal patch;
 g. be provided as IV solution for use in emergency medicine;
 h. be formulated for use as an IM injection;
 i. be formulated to be compatible with parenteral feeding;
 j. be provided in a suppository format
 k. be provided in dissolvable, impregnated oral strips;
 l. be delivered as a dissolvable strip placed on the tongue;
 m. be delivered in a soluble bi-layer gel capsule; and
 n. be used as a flavoring or fragrance.

GLOSSARY

SIRTS: Silent information regulator/Sirtuin genes
FOXO: Forkhead proteins
cAMP: Cyclic adenosine monophosphate
CREB: cAMP response element binding
CREM: cAMP response element modulator
Ppar: Peroxisome proliferator activated receptor
FAD: Flavin adenine dinucleotide
GTP: Guanosine triphosphate
NAD(P)H: Nicotinomide adenine dinucleotide phosphate

What is claimed is:

1. A method of treating a patient afflicted with Diabetes Mellitus to reduce HbA1c of said patient in which energy is provided to energy deprived cells of said patient, said method consisting of administering, to said patient afflicted with said Diabetes Mellitus, a therapeutically effective amount of methyl pyruvate and ethyl pyruvate together with at least one additional agent, so as to provide said energy to said energy deprived cells via a citric acid cycle and so as to reduce said HbA1c of said patient;
 wherein said at least one additional agent is selected from the group consisting of acetyl L-carnitine, taurine, inosine, magnesium chloride, magnesium L-threonate, alpha lipoic acid, vitamin E in the form of alpha and gamma tocopherol, vitamin D3 and niacin.

2. The method according to claim 1, wherein said therapeutically effective amount of said methyl pyruvate and said ethyl pyruvate ranges is from about 1 microgram to about 100 grams at least once a day.

3. The method according to claim 1, wherein said therapeutically effective amount of said methyl pyruvate and said ethyl pyruvate ranges from about 1 microgram to about 50 grams per day and is administered in divided doses more than once a day.

4. The method according to claim 1, wherein said therapeutically effective amount is from about 1 to about 4 grams per day in eight ounces of water per gram of said methyl pyruvate.

5. The method according to claim 1, wherein said therapeutically effective amount comprises 2 grams of said methyl pyruvate at least once a day, said methyl pyruvate being diluted in water at a concentration of one gram of said methyl pyruvate per liter of water.

6. The method according to claim 1, wherein said administration provides said energy for the citric acid cycle that bypasses any prior cellular/mitochondria preparation.

7. The method according to claim 6, wherein said provided energy upregulates cellular crosstalk and networking.

8. The method according to claim 6, wherein said provided energy allows said energy depleted cells to proceed to a homeostatic state.

9. The method according to claim 1, wherein said provided energy increases the manufacture of proteins, lipids, and hormones via the mRNA at the ribosomes of the endoplasmic reticulum.

10. The method according to claim 1, wherein said provided energy increases ATP in said energy deprived cells, and wherein said increased ATP upregulates and restores specific cellular function of said energy deprived cells.

11. The method according to claim 1, wherein said provided energy diminishes inflammation in said cells.

12. The method according to claim 1, wherein said provided energy allows said energy deprived cells to manufacture insulin, said manufactured insulin reducing elevated blood glucose levels, and said reduction of said elevated blood glucose levels reduces said HbA1c in said patient.

13. The method according to claim 1, wherein said administration decreases blood glucose levels by causing a reduction of posttranslational phosphorylation of FOXO1, 3a, and 4.

14. The method according to claim 1, wherein said administration allows said energy deprived cells to restore the glucose transporter system (Glut4).

15. The method according to claim 1, wherein said administration improves insulin resistance of said energy deprived cells.

16. The method according to claim 1, wherein said provided energy restores the pharmacological capability and function of pharmaceutical ligands.

17. The method according to claim 1, wherein dosages of said methyl pyruvate and ethyl pyruvate are dependent on factors relating to said patient, and wherein said factors include co-morbid disease, BMI, and/or physical activity level of said patient.

18. The method according to claim 1, wherein said methyl pyruvate and ethyl pyruvate are administered with said inosine.

19. The method according to claim 1, wherein said methyl pyruvate and ethyl pyruvate are administered with said taurine.

20. The method according to claim 5, wherein said administration occurs at least once a week.

21. The method according to claim 2, wherein said therapeutically effective amount is 4 grams at least once a day, said methyl pyruvate being diluted in water at a concentration of one gram of said methyl pyruvate per liter of water.

22. The method according to claim 2, wherein said therapeutically effective amount is 4 grams diluted in water and administered twice a day.

23. The method according to claim 1, wherein the frequency of said administration depends on the physiological need of the patient.

24. The method according to claim 1, wherein said therapeutically effective amount comprises up to 200 g of said ethyl pyruvate per day and is orally administered in divided doses each day.

25. The method according to claim 1, wherein said therapeutically effective amount comprises from about 1 microgram to about 100 grams of said methyl pyruvate and is administered at least once a day.

26. The method according to claim 25, wherein said therapeutically effective amount comprises 50 grams of said methyl pyruvate at least once a day, said methyl pyruvate being diluted in water at a concentration of one gram of said methyl pyruvate per liter of water.

27. The method according to claim 25, wherein said therapeutically effective amount comprises 10 grams of said methyl pyruvate diluted in water once a day.

28. The method according to claim 1, wherein the administration is performed by administering:
a micronized freeze dried powder, a powder packet that is added to a water or other water based beverage, a frozen dessert, an oral gel mixture, being incorporated into a gum base that has a hard shelled immediate and time released delivery, into a time released transdermal patch, an IV solution, or by an intramuscular injection, a parenteral feeding, a suppository format, at least one impregnable oral strip that is dissolvable, at least one dissolvable strip placed on a patient's tongue, in a soluble bi-layer gel capsule, a flavoring agent, or a fragrance.

29. The method according to claim 1, wherein the administration takes place by one of the following routes:
ingestion of a frozen dessert or an oral gel mixture;
application of a timed releasing transdermal patch to the skin of the patient;
injection of an IV solution;
an intramuscular injection;
placing at least one impregnated oral strip that is dissolvable in the mouth of the patient;
placing at least one dissolvable strip on the tongue of the patient;
via a flavoring agent;
or via a fragrance.

30. A method of treating a patient afflicted with Diabetes Mellitus to reduce HbA1c of said patient, wherein energy is provided to energy deprived cells of said patient, said method consisting of:
a) administering, to said patient afflicted with said Diabetes Mellitus, a therapeutically effective amount of methyl pyruvate and ethyl pyruvate, so as to provide said energy to said energy deprived cells via a citric acid cycle in said cells and so as to reduce said HbA1c of said patient;
b) administering a plurality of additional agents together with said therapeutically effective amount of said methyl pyruvate and said ethyl pyruvate; and
c) monitoring glucose concentration of said patient suffering from said Diabetes Mellitus during said administration;
wherein said additional agents consist of alpha lipoic acid, acetyl L-carnitine, taurine, inosine, magnesium chloride, magnesium L-threonate, vitamin E in the form of alpha and gamma tocopherol, vitamin D3 and niacin.

* * * * *